US00PP15845P2

(12) United States Plant Patent
Bradford

(10) Patent No.: US PP15,845 P2
(45) Date of Patent: Jul. 12, 2005

(54) NECTARINE TREE NAMED 'ROSE BRIGHT'

(50) Latin Name: *Prunus persica*
Varietal Denomination: Rose Bright

(76) Inventor: Lowell Glen Bradford, 12439 E. Savana Rd., Le Grand, CA (US) 95333

( * ) Notice: Subject to any disclaimer, the term of this patent is extended or adjusted under 35 U.S.C. 154(b) by 105 days.

(21) Appl. No.: 10/738,338

(22) Filed: Dec. 18, 2003

(51) Int. Cl.[7] ..... A01H 5/00
(52) U.S. Cl. ..... Plt./190
(58) Field of Search ..... Plt./190

(56) References Cited

U.S. PATENT DOCUMENTS

PP3,165 P 5/1972 Anderson

PP7,421 P 1/1991 Bradford

*Primary Examiner*—Anne Marie Grunberg

(57) ABSTRACT

The present invention relates to a nectarine tree, *Prunus persica*, and more particularly to a new and distinct variety broadly characterized by a large size, vigorous, hardy, self-fertile, productive and regular bearing tree. The fruit matures under the ecological conditions described in early June, with first picking on Jun. 2, 2003. The fruit is uniformly large in size, somewhat acidic in flavor, globose in shape, clingstone in type, very firm in texture, yellow in flesh color, and almost full red in skin color. The variety was developed as a second generation cross using 'Red Diamond' (U.S. Plant Pat. No. 3,165) yellow flesh nectarine as the selected seed grandparent and 'Rose Diamond' (U.S. Plant Pat. No. 7,421) yellow flesh nectarine as the selected pollen grandparent.

1 Drawing Sheet

Botanical classification: *Prunus persica.*
Variety denomination: 'Rose Bright'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seedlings each year of these fruits, usually to reveal recessive characteristics. The present invention relates to a new and distinct variety of nectarine tree, which has been denominated varietally as 'Rose Bright'. During the 1990 blooming season I emasculated an entire Red Diamond (U.S. Plant Pat. No. 3,165) nectarine tree and applied pollen from Rose Diamond (U.S. Plant Pat. No. 7,421) nectarine. I harvested the fruit from that hybridization during the following summer, germinated their seeds, and grew them in my greenhouse. Upon reaching dormancy that fall, those seedlings were transplanted as a group to my experimental orchard located near Le Grand, Calif. in Merced County (San Joaquin Valley). From that group I selected one seedling that produced yellow flesh nectarines with good qualities and designated it as "18P240". During the spring of 1996 I gathered open pollinated seeds from "18P240", germinated and grew them as seedlings on their own root in my greenhouse, and transplanted them the following winter into a cultivated area of my experimental orchard described above as a group labeled "18P240 (OP)". During the spring of 1999 I selected the present variety as a single seedling from this "18P240 (OP" group. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is similar to its selected pollen grandparent, 'Rose Diamond' (U.S. Plant Pat. No. 7,421) nectarine by producing nectarines that are nearly globose in shape and yellow in flesh color and that mature during the first week in June, but is distinguished therefrom by producing nectarines that are clingstone instead of freestone, larger in size, darker red in skin color and more acidic in flavor.

The present variety is similar to its selected seed grandparent, 'Red Diamond' (U.S. Plant Pat. No. 3,165) nectarine, by producing nectarines that are nearly globose in shape, very firm in texture, yellow in flesh color and nearly full red in skin color, but is distinguished therefrom by producing fruit that matures about thirty days earlier and that is clingstone instead of freestone.

SUMMARY OF VARIETY

In summary, the present variety is characterized by a large size, vigorous, hardy, self-fertile, productive and regular bearing tree. The fruit matures under the ecological conditions described in early June, with first picking on Jun. 2, 2003. The fruit is uniformly large in size, somewhat acidic in flavor, globose in shape, clingstone in type, very firm in texture, yellow in flesh color, and almost full red in skin color.

DRAWING

The accompanying drawing is a set of three photographs selected to display the skin color, form, and size of the fruit and leaves and one photograph depicting flower buds, open blossoms and typical petals.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Jun. 6, 2003, on the original tree during its seventh growing season. All major color code designations are by reference to the Inter-Society Color Council, National Bureau of Standards. Common color names are also used occasionally.

TREE

Size: Large, reaching a height of 12' [3.7 m.] and a spread of 14' [4.3 m.] after seven growing seasons utilizing typical dormant pruning.

Vigor: Vigorous, responding typically to irrigation and fertilization. The variety grows about 3' [0.91 m.] of surplus top-growth during the spring and summer. The plant should be grown on a standard commercial rootstock for production purposes.

Growth: Spreading and dense.

Form: Pruned to a round top.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Very productive, thinning necessary.

Fertility: Self-fertile.

Bearing: Regular bearer with no alternate bearing yet observed.

Trunk:

- *Size.*—Large, with a maximum diameter of 10" [254 mm.] after the seventh growing season.
- *Texture.*—Shaggy.
- *Bark color.*—Dark brown [59. d.Br] with grayish brown [61. gy.Br] streaking.
- *Lenticels.*—Approximate number per square inch: 8. Color: Brilliant orange yellow [67. brill.OY]. Typical size: 3/16" to 7/16" [4.8–11.1 mm.].

Branches:

- *Size.*—Diameter of limb is 6" [152 mm.] measured 12" above the crotch, typical of *Prunus persica,* and dependent upon cultural practices and climatic conditions.
- *Texture.*—Smooth on 1st year wood, increasing roughness with age.
- *Color.*—1st year wood topside: Moderate red [15. m.R]. 1st year wood underside: Brilliant yellow green [116. brill.YG]. Older wood: Deep yellowish brown [75. deep yBr].
- *Lenticels.*—Approximate number per square inch: 80. Color: Light orange yellow [70. l.OY]. Typical size: 1/32" to 1/8" [0.8–3.2 mm.].

Leaves:

- *Size.*—Medium. Average length: 6" [152 mm.]. Average width: 1 3/8" [35 mm.].
- *Arrangement.*—Alternate.
- *Thickness.*—Medium.
- *Form.*—Elliptical.
- *Apex.*—Acuminate.
- *Base.*—Acute, with an average base angle of 65 degrees.
- *Surface.*—Smooth.
- *Color.*—Dorsal surface: Deep yellow green [118. deep YG]. Ventral surface: Strong yellow green [117. s.YG].
- *Margin.*—Finely serrate.
- *Venation.*—Pinnately net veined.
- *Vein color.*—Light yellow green [119. l.YG].
- *Petiole.*—Average length: 1/2" [12.7 mm.]. Average thickness: 1/16" [1.6 mm.]. Color: Brilliant yellow green [116. brill.YG].
- *Stipules.*—Number: 2 per leaf, up to 6 per growing tip. Average length: 5/16" [7.9 mm.]. Color: Light yellow green [119. l.YG] becoming Deep reddish brown [41. deep rBr] with maturity.
- *Glands.*—Number: Predominately 2 per leaf. Position: Both alternate and opposite, almost always positioned on the petiole. Size: Small. Form: Globose. Color: Brilliant yellow green [116. brill.YG] becoming dark reddish brown [44. d.rBr] in the center with maturity.
- *Leaf buds.*—Conic.

Flower buds:

- *Hardiness.*—Hardy, with respect to central California winters.
- *Diameter.*—Typically 5/16" [7.9 mm.] 1 week before bloom.
- *Length.*—Typically 1/2" [12.7 mm.] 1 week before bloom.
- *Form.*—Not appressed.
- *Surface.*—Pubescent.
- *Tip color.*—Strong purplish red [255. s.pR].

Flowers: Perfect, complete, perigynous, usually a single pistil, typically thirty or more stamens, five sepals and petal locations alternately positioned.

- *Type.*—Showy, large.
- *Average flower diameter.*—1 3/4" [44.5 mm.].
- *Number of petals.*—About 50% have only five, about 25% have additional smaller petals, and about 25% are double blossoms with ten fully sized petals.
- *Petal shape.*—Circular.
- *Petal margin.*—Somewhat wavy.
- *Average petal diameter.*—15/16" [23.8 mm.].
- *Average petal length.*—15/16" [23.8 mm.].
- *Petal apex.*—Rounded, with some having a shallow notch.
- *Petal base.*—Rounded to somewhat cordate.
- *Petal color.*—Pale pink [7. p.Pk] toward the apex smoothly blending to strong purplish pink [247. s.pPk] toward the base.
- *Anther color.*—Deep reddish orange [36. deep rO] over a brilliant yellow [83. brill.Y] center.
- *Stigma color.*—Light greenish yellow [101. l.gY].
- *Sepal color.*—Grayish purplish red [262. gy.pR].
- *Sepal length.*—9/32" [7.1 mm.].
- *Sepal width.*—1/4" [6.4 mm.].
- *Average pistil length.*—3/4" [19.1 mm].
- *Average stamen length.*—11/16" [17.5 mm.].
- *Fragrance.*—Moderate when nectar is present.
- *Blooming period.*—A few days earlie than average compared with other varieties.
- *Onset of bloom.*—One percent on Feb. 26, 2003.
- *Date of full bloom.*—Mar. 6, 2003.
- *Duration of bloom.*—One to two weeks, dependent on ambient temperature.
- *Number per cluster.*—1 to 3 with single flowers most common.

FRUIT

Maturity when described: Firm ripe, Jun. 6, 2003.
Date of first picking: Jun. 2, 2003.
Date of last picking: Jun. 14, 2003.
Size: Uniform, large for an early maturing variety.
*Average diameter axially.*—2½" [63.5 mm.].
*Average diameter across suture plane.*—2¾" [69.9 mm.].
*Typical weight.*—6.7 ounces [190 grams].
Form: Globose to somewhat oblate, some slightly asymmetrical.
*Longitudinal section form.*—Circular to elliptical.
*Transverse section through diameter.*—Circular.
Suture: A sharp groove from the stem to the shoulder, a shallow wedge-shaped trough along the side, a deep groove toward the apex ending about ½" [12.7 mm.] beyond the pistil point.
Ventral surface: Rounded, lipped on both sides toward the apex and base.
Lips: Sometimes unequal along the side, equal toward the apex.
Cavity: Flaring, elongated in the suture plane, suture showing on both sides, Light yellow [86. l.Y] stem markings typical.
*Depth.*—11/16" [17.5 mm.].
*Breadth.*—1" [25.4 mm.].
Base: Truncate.
Apex: Truncate, cordate when viewed along the suture.
Pistil point: Both apical and oblique, very short, depressed within the suture.
Stem: Medium.
*Average length.*—⅜" [9.5 mm.].
*Average width.*—3/16" [4.8 mm.].
Skin:
*Thickness.*—Medium.
*Surface.*—Smooth.
*Tenacity.*—Tenacious to flesh.
*Astringency.*—Slightly astringent.
*Tendency to crack.*—None observed in dry season.
*Color.*—Strong red [12. s.R] over most of the surface becoming very deep red [14. v.deep R] toward the apex with maturity, very small light yellowish brown [76. l.yBr] freckling on the sides toward the apex.
Flesh:
*Color.*—Brilliant yellow [83. brill.Y] with deep red [13. deep R] bleeding toward the skin and streaking toward the stone, increasing with maturity.
*Surface of pit cavity.*—Both light yellow [86. l.Y] and moderate red [15. m.R] fibers breaking when twisted from the stone.
*Amygdalin.*—Moderate.
*Juice.*—Abundant, rich.
*Texture.*—Very firm, crisp.
*Fibers.*—Abundant, fine.
*Ripens.*—Slightly earlier toward the apex and along the lips.
*Flavor.*—Moderately acidic with average sweetness, typically 12 brix.
*Aroma.*—Moderate.
*Eating quality.*—Good.

STONE

Type: Clingstone.
Form: Oval.
Hilum: Narrow, oblong.
Base: Straight.
Apex: Acute, with an average tip angle of 80 degrees.
Sides: Equal.
Surface: Irregularly furrowed toward the apex and pitted toward the base.
Ridges: Jagged toward the base.
External color: Moderate brown [58. m.Br].
Pit wall color when cracked: Strong yellowish brown [74. s.yBr].
Cavity surface color: Light yellowish brown [76. l.yBr].
Average pit wall thickness: ¼" [6.4 mm.].
Average width: 1 1/16" [27.0 mm.].
Average length: 1¼" [31.8 mm.].
Average breadth: 11/16" [17.5 mm.].
Tendency to split: Below average.
Kernel:
*Form.*—Oval.
*Skin color.*—Light orange yellow [70. l.OY] when freshly removed.
*Pellicle color.*—Moderate yellowish brown [77. m.yBr].
*Vein color.*—Deep yellowish brown [75. deep yBr].
*Taste.*—Sweet.
*Viable.*—Yes, if embryo-cultured.
*Average width.*—½" [12.7 mm.].
*Average length.*—⅝" [15.9 mm.].
*Amygdalin.*—Slight.

USE

Market: Fresh market and long distance shipping.
Keeping quality: Good. Fruit quality observed to remain in good condition after 21 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree, substantially as illustrated and described, that is most similar to its selected pollen grandparent, 'Rose Diamond' (U.S. Plant Pat. No. 7,421) nectarine, by producing nectarines that are nearly globose in shape and yellow in flesh color and that mature during the first week in June, but is distinguished therefrom by producing nectarines that are clingstone instead of freestone, larger in size, darker red in skin color and more acidic in flavor.

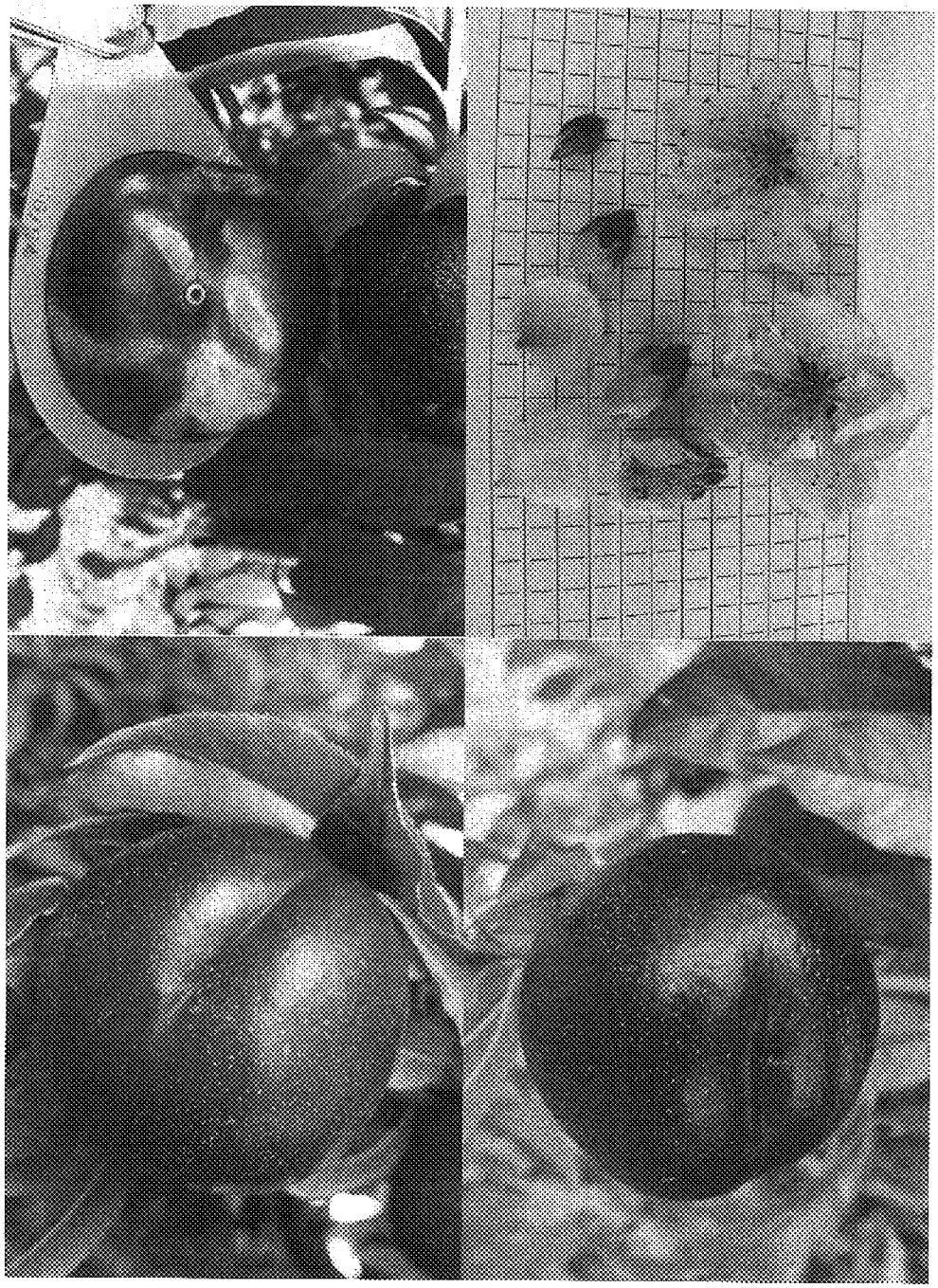

* * * * *